United States Patent
Vartdal et al.

(10) Patent No.: US 10,799,150 B2
(45) Date of Patent: Oct. 13, 2020

(54) IMAGE BASED BILIRUBIN DETERMINATION

(71) Applicant: PICTERUS AS, Trondheim (NO)

(72) Inventors: Gunnar Vartdal, Trondheim (NO); Lise Lyngsnes Randeberg, Trondheim (NO); Anders Aune, Trondheim (NO); Aleksander Kringstad, Trondheim (NO)

(73) Assignee: PICTERUS AS, Trondheim (NO)

( * ) Notice: Subject to any disclaimer, the term of this patent is extended or adjusted under 35 U.S.C. 154(b) by 100 days.

(21) Appl. No.: 16/065,103

(22) PCT Filed: Dec. 15, 2016

(86) PCT No.: PCT/NO2016/000030
§ 371 (c)(1),
(2) Date: Jun. 21, 2018

(87) PCT Pub. No.: WO2017/111606
PCT Pub. Date: Jun. 29, 2017

(65) Prior Publication Data
US 2019/0343426 A1    Nov. 14, 2019

(30) Foreign Application Priority Data
Dec. 22, 2015  (NO) .................... 20151783

(51) Int. Cl.
*A61B 5/103* (2006.01)
*G16H 50/50* (2018.01)
(Continued)

(52) U.S. Cl.
CPC .......... *A61B 5/1034* (2013.01); *A61B 5/1455* (2013.01); *A61B 5/14546* (2013.01);
(Continued)

(58) Field of Classification Search
USPC ....................................................... 382/128
See application file for complete search history.

(56) References Cited

U.S. PATENT DOCUMENTS 5,353,790 A  * 10/1994 Jacques ............. G01N 21/4738
                                                           250/574
10,285,624 B2 *  5/2019 Taylor ................. A61B 5/1034
(Continued)

FOREIGN PATENT DOCUMENTS

| JP | 2015009140 A | 1/2015 |
| KR | 20070063773 A | 6/2007 |

(Continued)

OTHER PUBLICATIONS

International Search Report (ISR) and Written Opinion of the International Search Authority (ISA) dated Apr. 28, 2017 in related Application No. PCT/NO2016/000030 (which was published as WO 2017/111606 A1 on Jun. 29, 2017).

(Continued)

*Primary Examiner* — Ishrat I Sherali
(74) *Attorney, Agent, or Firm* — Hershkovitz & Associates, PLLC; Abe Hershkovitz

(57) ABSTRACT

The invention relates to diagnosis in general and more specifically a system and a method for determining the presence of jaundice in newborn babies, also known as neonatal jaundice.
A main objective of the present invention is to provide a simple system and method for determining the presence of jaundice. Particularly since most deaths due to jaundice occur in low-income countries, there is a large unmet need of simple, reliable and affordable technologies able to identify at-risk newborn.
The objective is accomplished through receiving a depiction of skin from an RGB sensor, and then using either an optical diffusion model of the skin or Monte Carlo simulations to (Continued)

calculate the bilirubin concentration. A meta model of the optical diffusion model or Monte Carlo simulations can also be used. Colour calibration is also performed by e.g. thin-plate spline interpolation.

18 Claims, 8 Drawing Sheets

(51) Int. Cl.
*G16H 30/20* (2018.01)
*G16H 50/20* (2018.01)
*G16H 30/40* (2018.01)
*A61B 5/145* (2006.01)
*A61B 5/1455* (2006.01)
*A61B 5/00* (2006.01)

(52) U.S. Cl.
CPC ........... *A61B 5/4244* (2013.01); *G16H 30/20* (2018.01); *G16H 30/40* (2018.01); *G16H 50/20* (2018.01); *G16H 50/50* (2018.01); *A61B 2503/045* (2013.01); *A61B 2505/03* (2013.01); *A61B 2560/0242* (2013.01)

(56) References Cited

U.S. PATENT DOCUMENTS

2015/0057551 A1 2/2015 Hsu et al.
2015/0359459 A1 12/2015 Taylor et al.

FOREIGN PATENT DOCUMENTS

WO WO 2014/147149 A1 9/2014
WO WO 2014/172033 A1 10/2014

OTHER PUBLICATIONS

M. Aydin et al., "Neonatal Jaundice Detection System," *J. Med. Syst.*, (May 26, 2016), vol. 40, p. 166DE 2923106 A1.
G.F. Sudha et al., "Optical Monitoring of Bilirubin-Simulation and Experimental Results," *J. of Optics*, 2006, vol. 36, No. 2, pp. 87-97.
J.A. Delgado Atencio et al., "Monte Carlo Modeling of Light Propagation in Neonatal Skin," Applications of Monte Carlo Methods in Biology, Medicine and Other Fields of Science, Editor: Charles J Mode; Rijeka (HR): *In Tech*; Feb. 28, 2011, ISBN-13: 978-953-307-427-6.
English machine translation of KR 20070063773 A.
English language machine translation of JP 2015009140 A (Jan. 19, 2015).
Extended European Search Report in related Application No. EP 16879440, dated Jul. 4, 2019.

* cited by examiner

IMAGE BASED BILIRUBIN DETERMINATION

BACKGROUND OF THE INVENTION

1. Technical Field

The present invention relates to diagnosis in general, and more specifically, a system and a method for determining the presence of jaundice in newborn babies, also known as neonatal jaundice.

2. Background Art

In the prior art, traditional methods for analysis to determine the presence of jaundice are known, such as analysis of blood samples, and skin color analysis. The main problem with such prior art methods is cost and complexity, factors that rule out these methods from being affordable to much of the world, and also restrict these methods to centralized sites.

A more recent development in color analysis is provided by an application (hereinafter referred to as an "app") called Click Jaundice. This analysis is performed using a cell phone camera to capture a picture of a skin area as well as a color calibration chart placed within the area captured by the camera. The problem with this app is that it relies on a color calibration chart that must not be discolored, and also must have a central server that processes the pictures in view of how the color calibration chart has been reproduced by the camera. It is also important that the color calibration chart is correctly positioned with respect to angle and illumination in order to provide the correct information about the cell phone camera color reproduction.

Also, an app called Bilicam uses a similar system.

SUMMARY OF THE INVENTION

A main objective of the present invention is to provide a simple system and method for determining the presence of jaundice. Most deaths due to jaundice occur in low-income countries. There is therefore a large, unmet need for simple, reliable and affordable technologies that are able to identify an at-risk newborn.

The objective is achieved according to the invention by a method for determining the presence of jaundice.

That is, in a first embodiment, the present invention relates to a method for diagnosing a level of bilirubin concentration in blood causing jaundiced skin in a subject, comprising receiving a depiction of skin using a RGB sensor, comparing simulated skin colors of known bilirubin concentration with the received depiction, and calculating a level of bilirubin in the blood based on an optical diffusion model of a skin or Monte Carlo simulations of skin optics in the depiction.

The calculation of the level of bilirubin can be performed using a meta model of the diffusion model of skin or Monte Carlo simulations of skin optics.

Furthermore, the objective of the present invention is achieved by calibrating the color of the depiction of the skin using a color calibration chart.

In another embodiment, the present invention relates to a method for determining a rate of change in the level of bilirubin in blood causing jaundiced skin and sclera, comprising receiving a depiction using a RGB sensor of jaundiced skin and sclera with a color calibration chart, calculating a level of bilirubin concentration in the blood for skin and sclera, comparing the indicated level of bilirubin from the skin with the indicated level of bilirubin from the sclera, and determining a rate of change in the level of bilirubin in the blood by the difference in the indicated level of bilirubin from the skin to the indicated level of bilirubin from the sclera.

Yet another embodiment of the present invention relates to an apparatus for diagnosing a level of bilirubin concentration in blood causing jaundiced skin in a subject, which comprises means capable of receiving a depiction using a RGB sensor, of skin with a color calibration chart, and means for calculating a level of bilirubin based on an optical diffusion model of a skin or Monte Carlo simulations of skin optics in the received depiction.

In yet another embodiment, the present invention relates to a method for creating a customized treatment plan of a subject with jaundice by sunlight exposure wherein the data is obtained using a method for estimating a level of bilirubin concentration in blood causing jaundiced skin in a subject, comprising receiving a depiction of skin using a RGB sensor, and determining a level of bilirubin in the depiction by comparing simulated skin colors of known bilirubin concentration with the received depiction, wherein the simulated skin colors are obtained by using one of an optical diffusion model of a skin and Monte Carlo simulations of skin optics, or by using a color calibration chart, in combination with sunlight exposure data of a location or weather data, or in combination with sunlight exposure data of a location together with weather data.

A further embodiment of the present invention relates to a use of a method for estimating a level of bilirubin concentration in blood causing jaundiced skin in a subject comprising receiving a depiction of skin using a RGB sensor, and determining a level of bilirubin in the depiction by comparing simulated skin colors of known bilirubin concentration with the received depiction, wherein the simulated skin colors are obtained by using one of an optical diffusion model of a skin and Monte Carlo simulations of skin optics, or by using a color calibration chart, for creating a customized treatment plan of a subject with jaundice through sunlight exposure, wherein the data obtained using the method are combined with sunlight exposure data of a location or weather data, or are combined with sunlight exposure data of a location together with weather data.

In yet a further embodiment, the present invention relates to a calibration card or chart comprising a plurality of color patches, and wherein the calibration card further comprises a plurality of grey patches for detecting the variations of illumination of the calibration card.

Another embodiment of the present invention relates to a calibration card wherein the calibration card further comprises an opening through which the skin or sclera to be analyzed is visible when the calibration card is used in the received depiction.

In yet another embodiment, the present invention relates to a calibration card wherein the color patches on the calibration card are printed using spectral printing.

In a further embodiment, the present invention relates to a calibration card wherein the grey patches are evenly distributed over the calibration card.

In yet another embodiment, the present invention relates to a calibration card wherein at least one grey patch is arranged at a corner of the calibration card.

A number of other non-exhaustive embodiments, variants or alternatives of the invention are defined by the dependent claims.

The present invention attains the above-described objectives by depicting skin using a RGB sensor, and calculating a level of bilirubin based on an optical diffusion model of skin, or Monte Carlo simulations of skin optics.

Preferably, the sensor is calibrated using a calibration chart placed within view of the RGB sensor during the depiction of the skin. The calibration can be performed under varying light conditions, and using a color calibration chart that is known to be good.

The technical differences over prior art as represented by Click Jaundice and Bilicam is that the calculation of bilirubin level is based on an optical diffusion model of the skin, or Monte Carlo skin optics simulations. In addition, a meta model, a direct lookup table, or supervised machine learning techniques, are used on this model or simulations. The color calibration card is preferably printed using spectral printing to insure that the colors on the card changes similarly when subject to differing light sources or illumination conditions.

These effects in turn provide several further advantageous effects: the present invention makes it possible to use simple and low cost mass market cameras that are found in many cell phones, and makes it possible to use the model to accommodate different types of skin, such as different skin colors. In addition, the present invention makes it possible to use the model without a reliable internet connection.

BRIEF DESCRIPTION OF THE DRAWINGS

The above and further features of the invention are set forth with particularity in the appended claims and, together with advantages thereof, will become clearer from consideration of the following detailed description of an exemplary embodiment of the invention given with reference to the accompanying drawings.

The invention will be further described below in connection with exemplary embodiments which are schematically shown in the drawings, wherein.

DESCRIPTION OF THE REFERENCE SIGNS

Figure 1:
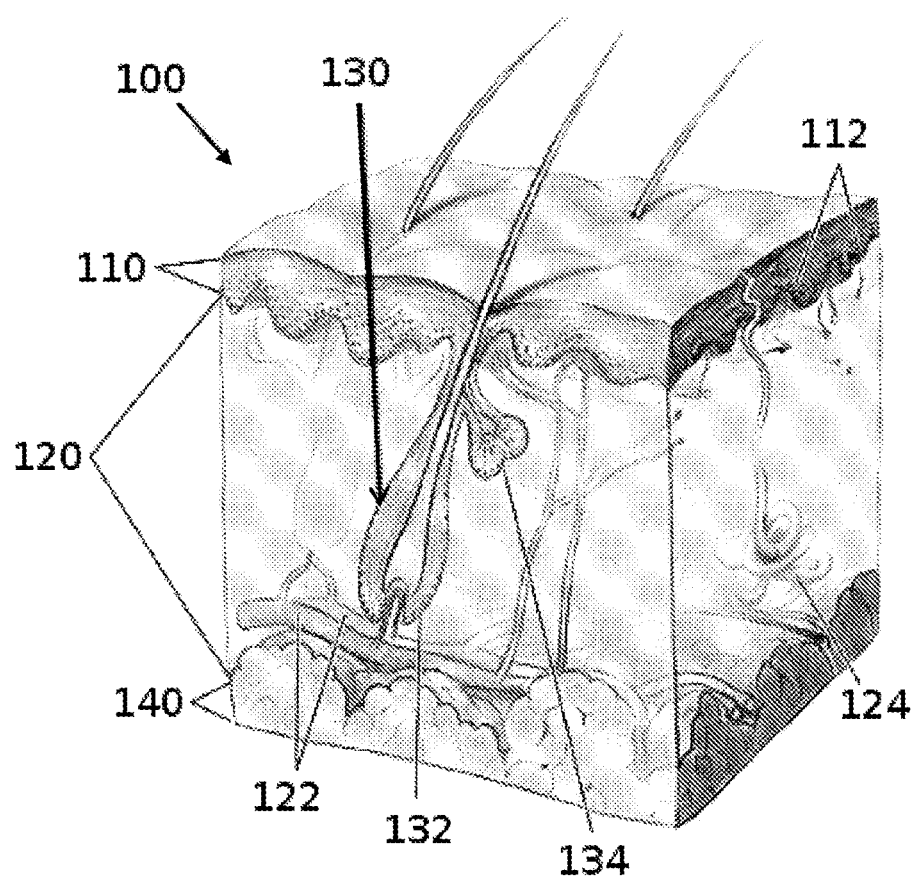
FIG. 1 shows a cross section of human skin.

The following reference numbers and signs refer to the drawings:

| | |
|---|---|
| 100 | Skin model |
| 110 | Epidermis |
| 112 | Melanocytes |
| 120 | Dermis |
| 122 | Blood vessels |
| 124 | Sweat gland |
| 130 | Hair follicle |
| 132 | Follicle |
| 134 | Oil gland/sebaceous gland |
| 140 | Fatty tissue |
| 221 | Extinction coefficients for oxygenated hemoglobin |
| 222 | Extinction coefficients for unoxygenated hemoglobin |
| 223 | Extinction coefficients for methemoglobin |
| 224 | Extinction coefficients for bilirubin |
| 231 | Transmission of red wavelength through a Bayer color filter array |
| 232 | Transmission of green wavelength through a Bayer color filter array |
| 233 | Transmission of blue wavelength through a Bayer color filter array |
| 234 | Transmission of camera infrared filter |
| 235 | Quantum efficiency of CMOS sensor |
| 241 | Red filter in a Bayer color filter array |
| 242 | Green filter in a Bayer color filter array |
| 243 | Blue filter in a Bayer color filter array |
| 441 | Simulated skin color |
| 442 | HTC: White balance auto |
| 443 | HTC: White balance daylight |
| 444 | S3: White balance auto |
| 445 | S3: white balance daylight |
| 461 | HTC One V |
| 462 | iPhone 5 |
| 463 | Samsung Galaxy S3 |
| 471 | Skin simulations for increasing levels of bilirubin |
| 472-475 | Color difference measured of bruised and non-bruised skin |
| 500 | Color calibration card |
| 502 | Opening |
| 504 | Grey field |
| 506 | Color patch |

DETAILED DESCRIPTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

Jaundice is a condition characterized by the skin of the afflicted turning yellow. This is due to elevated levels of the waste product bilirubin in the blood leaking into skin tissue. The condition is therefore often called hyperbilirubinemia. It is a condition affecting approximately half of all newborns, but is in most cases harmless. The condition is still potentially dangerous because the bilirubin can accumulate in the basal ganglia of the brain, where it can cause permanent brain damage. Such brain damage, better known as kernicterus, can manifest itself as cerebral palsy, deafness, language difficulty, or in the worst cases, death [1].

To prevent the usually harmless condition of jaundice from developing into kernicterus, it is highly important to identify the children at risk at an early stage. Treatment of hyperbilirubinemia is in most cases done by phototherapy, and in some extreme cases by blood transfusion. Sunlight is believed to be a cheap alternative to specialized phototherapy light-boxes, and studies are now underway investigating this [3]. It is therefore essential to be able to discover at-risk children at an early stage, so that effective treatment can be given.

The growing use of smartphones also makes it possible to create customized treatment plans for neonatal jaundice using sunlight based on geolocation services on the smartphones. Using the GPS and other information, e.g., weather data from the smartphone, one can give recommendations on when, for how long, and how often patients need to be in the sun to get effective treatment. This can be calculated by looking at when the sunlight has a maximum amount of light in the wavelengths (~450 nm wavelength) that provide treatment for jaundice, while at the same time, has the minimum amount of damaging UV-radiation. This can be done by combining information from publicly available UV-index forecasts and spectral sunlight irradiance calculators for solar panels [42]. This can be combined with a low-cost diagnostic tool to provide customized low-cost treatment as well.

Bilirubin colors the skin yellow. Jaundice can therefore often be seen visually even by people with no medical training, but mere visual judgment of the severity of jaundice has proven to be unreliable, even when performed by experienced doctors [4]. The measurement of bilirubin is therefore traditionally done by blood samples. To reduce the need of drawing blood from a newborn, devices have been developed that measure the bilirubin concentration by shining light through the skin, so-called transcutaneous bilirubinometers [5]. Both the lab equipment needed for blood sample measurements and the devices used to measure bilirubin transcutaneously are expensive, costing more than 10,000 US dollars, thus making them practically unavailable in low-income countries.

Skin 100 is the human organism's barrier to the environment. It is a structure composed of different layers. The top layer, called the epidermis 110, is typically 100 micrometres thick and contains among other things the pigment melanin, which is the pigment responsible for the different skin colors of the world. Below the epidermis lies the dermis 120, which has a typical thickness of 1-4 mm. In the dermis, among other things, blood vessels 122, connective tissue, sweat glands 124 and hair follicles 130, and sensory nerve systems are found. The hair follicle 130 comprises a follicle 132 that surrounds a hair and further comprises an oil gland 134, also known as a sebaceous gland that produces sebum. The subcutaneous fatty layer 140 lies below the dermis, and provides insulation and protection from mechanical stress. FIG. 1 illustrates the different skin layers along with some of the components found in the skin.

Light hitting biological tissue, such as skin, is either scattered or absorbed. The intensity of light able to penetrate into the tissue is given by the Beer-Lambert law, $$I(x)=I(0)e^{-\mu_{tr}x} \quad (2.1)$$

where $I(0)$ is the incident light intensity, x is the distance traveled in the tissue and $\mu_{tr}$ is the transport coefficient, or the total attenuation coefficient. The transport coefficient can be written as the sum of the reduced scattering coefficient, $\mu'_s$, and the absorption coefficient, $\mu_a$.

The scattering coefficient $\mu_s$ describes the amount of light that is scattered by the tissue. Some of this light is scattered in a forward direction, not decreasing the penetrating light's intensity. The reduced scattering coefficient incorporates this by being expressed as $\mu'_s=\mu_s(1-g)$, where g represents the amount of light scattered in a forward direction. g is called the anisotropy factor, and is calculated as the average of the cosine of the scattering angle distribution, $$g=\text{avg}(\cos(\theta)). \quad (2.2)$$

In skin, the anisotropy factor is approximately equal to 0.8, indicating highly forward directed scattering.

Skin contains several different molecules responsible for the absorption and scattering of incident light. The properties of these molecules and the surrounding tissue are presented in the following sections.

Skin, as just mentioned, contains many absorbing and scattering molecules. The main absorber in the epidermis is melanin [7]. Skin types based on varying amounts of the pigment melanin can be classified by the Fitzpatrick skin type scale I-VI [8]. On this scale, type I refers to very fair skin that sunburns and does not tan, while type VI is at the opposite end of the scale, referring to very dark skin.

Melanin absorbs light of wavelengths ranging from ultraviolet to near-infrared. The wavelength dependence of the absorption is reported as $\lambda^{-3.46}$ [9]. The absorption of melanin across the whole spectrum can therefore be defined by the absorption at a single wavelength. Absorption can be measured at 694 nm, and absorption values in adults have been found to vary from 300 m$^{-1}$ for fair Caucasian skin to 2500 m$^{-1}$ for dark African skin [10]. Newborn skin is reported to have lower concentrations of melanin than adult skin [11]. Here, it is therefore assumed that the melanin absorption of newborn skin at 694 nm does not exceed 2000 m$^{-1}$, although exact numbers have not been found in the literature.

Figure 2:
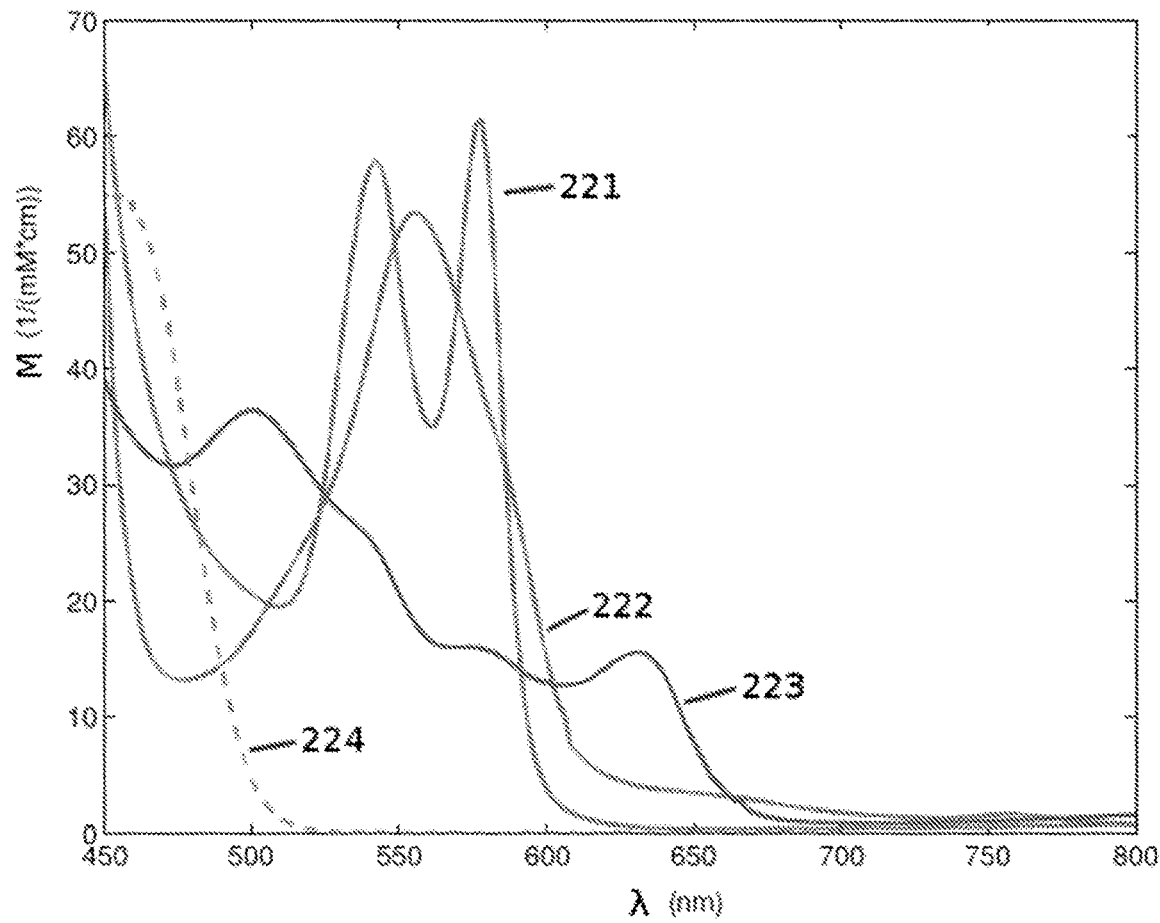
FIG. 2 shows extinction coefficients for hemoglobin, methemoglobin and bilirubin.

The main absorbers in blood are oxygenated and deoxygenated hemoglobin. Methemoglobin can also be formed if hemoglobin is exposed to oxidative stress, but is generally found in low concentrations. Exceptions are, e.g., drug use, which can lead to methemoglobinemia [12]. The absorption spectra of hemoglobin 221, deoxyhemoglobin 222 and methemoglobin 223 can be seen in FIG. 2. The spectra of hemoglobin and deoxyhemoglobin can be seen intersecting at several points. Such points are called isosbestic points. Measuring hemoglobin concentrations is often done at isosbestic wavelengths because the total measured concentration will not depend on the oxygenation level of the blood [13].

Bilirubin is the breakdown product of heme catabolism [14]. Heme is found in hemoglobin and myoglobin. Bilirubin 224 causes skin to turn yellow if it is allowed to accumulate in the dermis, due to its high absorption of the shorter wavelengths of the visible spectrum (see FIG. 2). This is also the reason for the yellow color seen in old bruises [15], as macrophages are recruited to the area of the bruise where it phagocytizes erythrocytes and hemoglobin molecules, catabolizing the hemoglobin to bilirubin [16].

The yellow color from bilirubin can also be seen across the whole body, and is then caused by either a high turnover rate of hemoglobin, or liver failure, or both. Newborns acquire jaundice due to a high turnover rate of hemoglobin after birth. An elevated concentration of bilirubin in combination with a not fully developed blood-brain barrier can lead to permanent brain damage or death [17]. For this reason, 5-10% of all newborns receive either phototherapy, or in extreme cases, blood transfusion to rid the body of the excess bilirubin [14].

Bilirubin in blood is bound to albumin. In this form, the combined molecules are too big to pass the blood vessels. When bilirubin concentrations exceed 400-500 micromolar, there is not enough albumin to bind all the bilirubin molecules [17]. The free bilirubin can then diffuse through the blood vessels and into the surrounding tissue. The skin concentration of bilirubin is therefore markedly lower than the blood serum concentration. Good correlation has been found between the skin concentration of bilirubin measured by transcutaneous bilirubinometers and the total blood serum concentration [18]. This makes it possible to estimate the blood serum concentration through transcutaneous bilirubin measurements.

Transcutaneous bilirubinometers measure the bilirubin concentration by shining light of certain wavelengths and wavelength ranges into the skin. The reflected light of each wavelength is measured and used to calculate the concentration. Full reflection spectroscopy of newborns can similarly be used to measure bilirubin concentration. In addition, the reflected spectrum allows the calculation of several other parameters, such as melanin concentration and the gestational age of the newborn. For details of how such measurements are performed, one should refer to a patent for a transcutaneous bilirubinometer [19] and a paper by Randeberg et al. [20].

As for other absorbers, one should refer to carotenoids, which are organic pigments found in plants. These pigments cannot be produced by animals, so they are obtained through diets. They all absorb light in the wavelength range 400-550 nm. A common carotenoid abundant in carrots, beta carotene, has a double peak in its absorption spectrum at 450 and 480 nm, giving it a yellow/orange color. This color, which is similar to the color of bilirubin, could potentially be an error source in bilirubin measurements. However, the skin concentration of all carotenoids is generally too low to have an impact, especially in newborns that do not eat carotenoids themselves [7, p. 10]. They only get carotenoids through milk.

Water should also be mentioned because it is found in abundance in skin. However, water has low absorption in the visible spectrum with a minimum at 418 nm and increasing absorption for wavelengths above 600 nm [21]. The water content of skin is therefore not explicitly accounted for.

Large molecules such as collagen fibres are a major source of scattering in the dermis. These molecules, and changes in the refraction index between them and the surrounding tissues, are responsible for the fact that scattering is the dominating process in this tissue. The epidermis has similar scattering properties, but absorption due to melanin can in some cases be the dominating process in this layer. Bashkatov [6] showed that the reduced scattering coefficient of skin in the wavelength range of 400 to 2000 nm can be expressed as $$\mu'_s = 73.7\lambda^{-0.22} + 1.1 \cdot 10^{12} \lambda^{-4}. \quad (2.3)$$

Background tissue absorption is absorption caused by other molecules than the ones mentioned in the above sections. This value is set to $\mu_n = 25$ m$^{-1}$ [22] for both the epidermis and the dermis. This value is similar to what is found in ocular (eye) tissue.

One mathematical model used for numerical simulations in this invention is based on optical diffusion theory. Optical diffusion theory can be applied when scattering dominates over absorption [23]. This theory has limited validity in thin layers, and finding appropriate boundary conditions is problematic. Optical diffusion theory does not apply to air, but Haskell et al. [24] discovered boundary conditions that can be used for interfaces such as those between air and tissue, giving good results of simulations of diffuse skin reflectance [22]. Monte Carlo methods are also known to be accurate for simulations of skin optics, but they are also much more computationally expensive [25]. Given enough computational time, Monte Carlo simulations could be performed to be used to model the skin optics necessary to estimate bilirubin levels from skin color.

For the simulations performed in the present invention, the skin is modelled as consisting of three flat layers. The top layer represents the epidermis. To account for the papillary structure between the dermis and epidermis, as seen in FIG. 1, blood is included in the epidermis. The epidermis therefore contains both blood and melanin in the model. The middle layer represents the top part of the dermis, and the bottom layer is a layer extending infinitely downwards. All molecules are modelled as uniformly distributed within each layer. The total transport coefficients of each layer can thus be calculated based on the background tissue scattering and absorption described earlier, and the concentrations of the different light absorbing molecules. These transport coefficients can then be used in the diffusion model of skin developed by Svaasand et al. [22]. A summary of which will be presented below.

Svaasand et al. [22] starts by assuming an almost isotropic light distribution and by expressing the radiance L by a series expansion, $$L = \phi/4\pi + \tfrac{3}{4}\pi j \cdot I + \quad (2.4)$$

where φ and j are the fluence rate and the diffuse photon flux vector respectively. I is the direction of the deviation from isotropy in the light distribution. The irradiance on a surface normal to the flux then becomes $$E = \phi/4 \pm j/2. \quad (2.5)$$

where the sign is plus for surfaces against the flux and minus for surfaces along. The diffuse photon flux vector is given by, $$j = -D\nabla\phi \quad (2.6)$$

with the diffusion constant, $$D = \tfrac{1}{3}\mu_{tr}. \quad (2.7)$$

The continuity equation can then be expressed as, $$\nabla \cdot j = -\mu_a \phi + q \quad (2.8)$$

where q is the source density of diffuse photons. The combination of equations 2.6 and 2.8 yields, $$\nabla^2 \phi - \phi/\delta^2 = -q/D \quad (2.9)$$

where $\delta = \mathrm{sqrt}(1/(3\mu_{tr}\mu_a))$ is the optical penetration depth.

The boundary conditions between two scattering media is then expressed by the continuity of irradiance in the forward and backward directions, $$\frac{\phi_1}{4} \pm \frac{j_1}{2} = \frac{\phi_2}{4} \pm \frac{j_2}{2}. \quad (2.10)$$

Haskell et al. found that a very useful boundary condition at the skin-air interface is obtained by relating the reflected part of the irradiation at the inside of the interface to the irradiation propagating back into the skin [24]

$$R_{eff}\left(\frac{\phi}{4} + \frac{j}{2}\right) = \frac{\phi}{4} - \frac{j}{2} \quad (2.11)$$

where $R_{eff}$ is the effective reflection coefficient. The value of $R_{eff}$ can be found by integrating the Fresnel reflection coefficient for unpolarized light over all angles of incidence.

For an isotropic light distribution, the source density functions of Equation (2.9) are expressed as functions of the light intensity, $P_0$, transmitted through the skin-air interface as $$q_1 = P_0 \mu'_{s,1} e^{-\mu_{tr,1} x}$$

$$q_2 = P_0 \mu'_{s,2} e^{-\mu_{tr,1} d_1} e^{-\mu_{tr,2}(x-d_1)}$$

$$q_3 = P_0 \mu'_{s,3} e^{-\mu_{tr,1} d_1} e^{-\mu_{tr,2} d_2} e^{-\mu_{tr,3}(x-d_1-s_2)} \quad (2.12)$$

where the indices 1, 2 and 3 represent each layer, d represents the thickness of a layer, and x the distance from the skin surface.

The solutions to equation (2.9) using these source equations can then be written as $$\phi_1 = \frac{P_0 \delta_1^2 \mu'_{s,1}}{D_1(1-\mu_{tr,1}^2 \delta_1^2)} e^{-\mu_{tr,1} x} + A_1 e^{-\frac{x}{\delta_1}} + A_2 e^{\frac{x}{\delta_1}} \quad (2.13)$$

$$\phi_2 = \frac{P_0 \delta_2^2 \mu'_{s,2}}{D_2(1-\mu_{tr,2}^2 \delta_2^2)} e^{-\mu_{tr,1} d_1} e^{-\mu_{tr,2}(x-d_1)} + A_3 e^{-\frac{x}{\delta_2}} + A_4 e^{\frac{x}{\delta_2}}$$

$$\phi_3 = \frac{P_0 \delta_3^2 \mu'_{s,3}}{D_3(1-\mu_{tr,3}^2 \delta_3^2)} e^{-\mu_{tr,1} d_1} e^{-\mu_{tr,2} d_2} e^{-\mu_{tr,3}(x-d_1-d_2)} + A_5 e^{-\frac{x}{\delta_3}}.$$

The values of the constants $A_1$-$A_5$ can then be found by applying the boundary conditions of equations (2.10) and (2.11). After this, the diffuse reflection coefficient can be calculated by $$\gamma = \frac{j|_{x=0}}{P_0}. \quad (2.14)$$

For the complete expression for $\gamma$, see, for example, the appendix of Svaasand et al. [22].

These calculations and simulations of skin optics can be used to calculate the total reflected spectrum from skin with different amounts of blood, melanin, bilirubin, and all other aforementioned parameters. These simulated reflection spectra can then be used to calculate the skin colors these spectra represent by employing the standards defined by the International Commission on Illumination [26].

Estimating Skin Parameters From Measured Color

Searching through the space of input skin parameters by simulating skin color for each set of input parameters to find a color that matches with the measured color is extremely time consuming using the simulation methods described above. An alternative method of estimating the skin parameters from a measured color that is both fast and requires a reasonably small amount of disk space is therefore needed.

Estimating the input skin parameters from a measured color can be performed efficiently through inverse meta modelling of the skin simulations or through supervised machine learning techniques such as regression methods and neural networks. The inverse meta model is a surrogate model of the skin simulations that map the output of the skin simulations to their input skin parameters. This meta model can be created by employing several different regression methods, or in some cases through a direct lookup table, or a combination of the two. Partial least squares-based regression models (PLSR) are recommended for inverse meta modelling of this kind [40]. For a detailed description of the PLSR meta modelling technique, see, for example, appendix A of [40]. An advantage with using supervised machine learning methods, e.g. neural networks or standard regression methods, is that a system can be created that is able to use colors from an device-independent color space, such as the calibrated colors from pre-recorded images, and map these colors to their most likely corresponding bilirubin values. This alternative to creating a meta-model has been described earlier hereinabove.

Several input skin parameters can result in approximately the same output colors from the simulations (called "sloppiness"). This makes it difficult to use regression-based methods such as PLSR. This sloppiness can be handled by employing the method of hierarchical cluster-based partial least squares regression (HC-PLSR). HC-PSLR works by first creating a global PLSR model [42]. This model is then separated into clusters either by prior knowledge of the data or by algorithms such as fuzzy clustering [41]. A local PLSR model is then created for each cluster. The input skin parameters can then be estimated from a measured color by using the global PLSR model to find the cluster the color most likely belongs to, and then using the PLSR model created for that model to predict the input skin parameters. If the number of clusters in the HC-PLSR model equals the number of skin simulations performed to train the model, the method becomes a direct lookup method.

As the direct lookup method requires both the largest amount of disk space, and usually the longest computational time to perform, it should only be used when it is known that the hardware that runs the algorithm is capable of handling both the disk storage and the computational demand. If disk storage space and computational demand become an issue, the HC-PLSR method should be employed. For lower-end hardware, a small number of clusters in the HC-PLSR method should be used, and vice versa.

Another way of reducing the sloppiness of the simulations is to search for the colors that have the highest probability of occurring around a measured color. As many of the input parameters to the numerical skin model are normally distributed, one can use the mean and the standard deviation of these parameters found in the literature to find which input parameters are the most likely to produce the measured color. The color calibration error could be used as a measure of how far away from the measured color one should search for probable input parameters.

Color Calibration

The eye has three types of cone cells which are sensitive to light of varying wavelengths. These cone cells provide the sensory input needed for color perception. One type of cone cell primarily absorbs light of shorter, blue, wavelengths, and the other two absorb mainly green and mainly red, respectively. Nevertheless, there is significant overlap between the sensitivity spectra of the cells. Three parameters corresponding to the stimulus values provided by the cone cells can therefore be used to describe any perceivable color.

Almost all smartphone cameras today include a CMOS (Complimentary Metal-Oxide Semiconductor) sensor. These sensors have arrays of photodiodes that generate current when photons are absorbed. The efficiency with which the photodiodes generate current depends on the wavelength and is called the quantum efficiency. A typical quantum efficiency of a CMOS sensor can be seen as the line 235 in FIG. 3.

On top of the CMOS sensor is a color filter array. A single cell in a color filter array covers a single photodiode and transmits only wavelengths of a certain color to this diode. A commonly used filter of this type is the Bayer filter array. The Bayer filter array contains 50% green, 25% red and 25% blue filters. This is to resemble the human eye's increased sensitivity to the intensity of green light. The filters are placed in a specific pattern, as can be seen in FIG. 4, and their transmission frequencies can be seen in FIG. 3.

Figure 3:
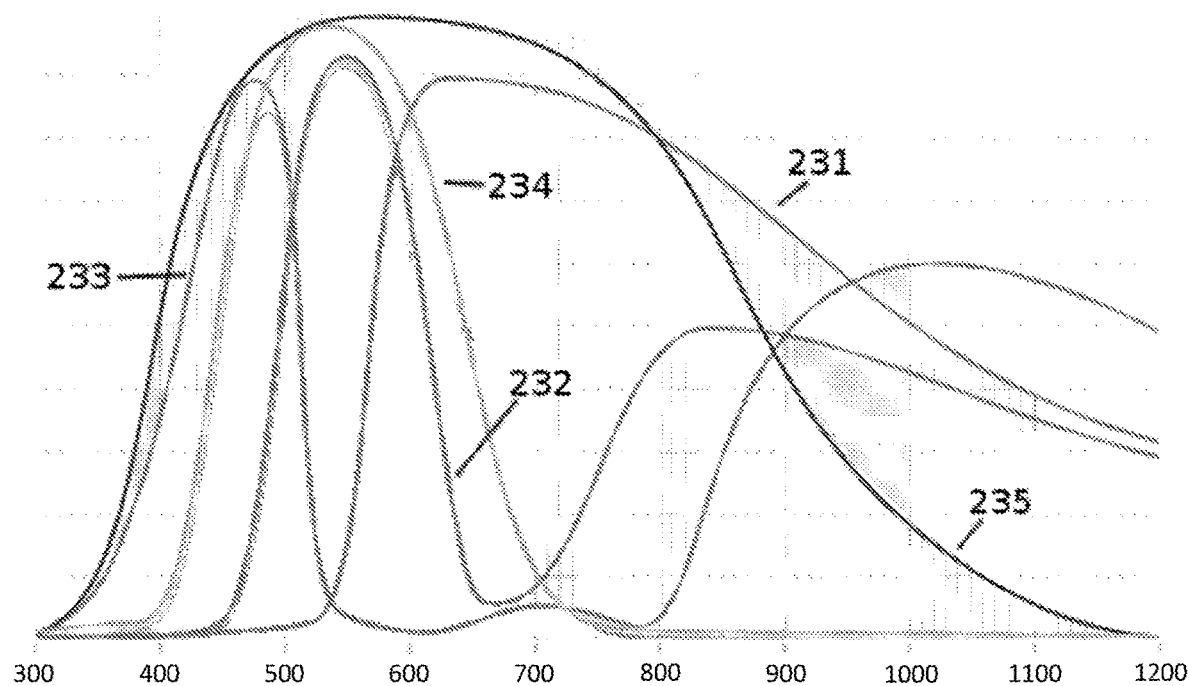
FIG. 3 shows the quantum efficiency of a CMOS sensor through a Bayer color filter array.
Figure 4:
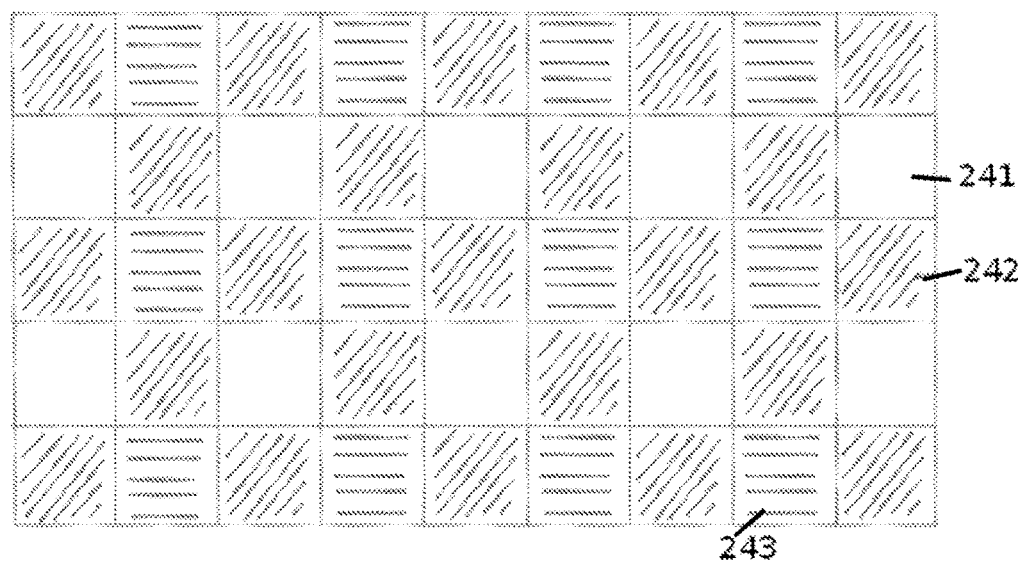
FIG. 4 shows positions of the red, green and blue color filters in a Bayer filter array.

FIG. 3 shows transmissions of red 231, green 232 and blue 233 wavelengths through a Bayer color filter array. Cameras are typically provided with an infrared filter having a transmission 234 shown in the same figure. Also shown is the quantum efficiency 235 of a CMOS sensor.

This type of filter arrangement creates in effect three different images, one red, one green and one blue. All three of these images are collectively called a raw format image. High end digital cameras have the option to output images in this format. Less expensive cameras, including smartphone cameras, do not have this option. In these cameras, the three original images are combined using a demosaicing algorithm, interpolating the missing red, green or blue pixel values from the surrounding pixels. This process can be done by both hardware and software, and the specific algorithms used differ for the different cameras. The result of this process in smartphones is a JPEG image with RGB values for each pixel in the sRGB color space.

White balance adjustments of the image are also performed in addition to the demosaicing algorithm. These color adjustments are performed to attempt to recreate the colors of the scene more accurately. The process is called white balance because photographers often use images of known white or grey objects as references when performing these adjustments. The images need such color adjustments because the light source illuminating the scene will create different color responses in the camera depending on the light source used. Cameras therefore often come preset with white balance settings such as daylight, cloudy, incandescent and fluorescent to accommodate for common light sources. The cameras also have an auto white balance setting which adjusts the colors of the images automatically depending on the distribution of colors in the image.

The white balance mode can be set using the smartphone camera app on almost all smartphones. Other settings, such as the shutter speed, which is the amount of time the camera allows light to reach the sensor, can only be set on a few smartphones. This lack of control over camera settings could pose a challenge because small changes in, e.g., the light intensity of a scene, could potentially alter the image substantially.

White balance adjustments can create images that look good, but that does not mean that colors are reproduced accurately. To achieve good color reproduction, images of objects with known colors can be captured. The colors of the captured images can then be adjusted according to the known colors of this color target. A common target used in photography settings is the Macbeth ColorChecker [27]. The ColorChecker contains 24 squares of different colors. The upper half contains colors often found in nature, while the bottom half contains a grey scale and colors close to the primary colors of the RGB and CMY color spaces.

Two different calibration methods have been tested, both of which are presented in the following.

Ilie et al. [28] tested three different methods for the color calibration of images. The first was a linear least squares matching, the second was a linear RGB to RGB matrix transformation, and the third was a general polynomial transform. Of these, the general polynomial transform was found to be the most accurate because it was the only method that could account for both linear and non-linear error sources. It was therefore chosen to be implemented here.

The equation for the general polynomial transform for color channel $c \in \{r, g, b\}$ of sample color s is $$\sum_{k=1}^{D} (t_{rc_k} Ir_s^k + t_{gc_k} Ig_s^k + t_{bc_k} Ib_s^k) + t_{c_0} \simeq Tc_s \quad (2.22)$$

where D is the degree of the polynomial approximation. $Ir_s^k$, $Ig_s^k$ and $Ib_s^k$ are the red, green and blue sample color values of the captured image raised to the power of k, while $Tc_s$ is the true value of the target color sample s. $t_{xc_k}$ is the polynomial coefficient of order k, specifying the influence of the input color channel $x \in \{r, g, b\}$ on the output color channel c. For D=2 with 24 color samples, such as when using the ColorChecker, equation 2.22 can be written in matrix form as $$\begin{bmatrix} Ir_1 & Ir_1^2 & Ig_1 & Ig_1^2 & Ib_1 & Ib_1^2 & 1 \\ Ir_2 & Ir_2^2 & Ig_2 & Ig_2^2 & Ib_2 & Ib_2^2 & 1 \\ \ldots & \ldots & \ldots & \ldots & \ldots & \ldots & \ldots \\ Ir_{24} & Ir_{24}^2 & Ig_{24} & Ig_{24}^2 & Ib_{24} & Ib_{24}^2 & 1 \end{bmatrix} \times \begin{bmatrix} t_{rc_1} \\ t_{rc_2} \\ t_{gc_1} \\ t_{gc_2} \\ t_{bc_1} \\ t_{bc_2} \\ t_{c_0} \end{bmatrix} \simeq \vec{T}c_s \quad (2.23)$$

This equation can be solved for the polynomial coefficients, $t_{ck}$, by calculating the pseudo-inverse of the matrix, B, containing the input sample color values. The equation to be solved is therefore $$B \times \vec{t}_{c_k} \simeq \vec{T}c_s \leftrightarrow \vec{t}_{c_k} \simeq \text{Pinv}(B) \times \vec{T}c_s \quad (2.24)$$

resulting in a vector $t_{ck}$ that can be used to convert any input color from the input color space to the calibrated color space. The equations outlined here assume usage of a RGB color space, but the method can be used for any three-dimensional vector space, including the XYZ color space.

Menesatti et al. [29] compares a commonly used commercial color profiling tool called ProfileMaker to a novel calibration procedure using thin-plate spline interpolation. The thin-plate spline method was found to give significantly better calibration results.

The thin-plate spline interpolation method is named after the physical analogy of bending thin metal plates to fit to certain fixed coordinates [30]. It is used in the field of medical imaging, as a means of transforming and analyzing images from, e.g., magnetic resonance imaging (MRI) scans [31]. In three dimensions, the method works by finding a function $f(x_1, x_2, x_3)$ that minimizes $$\frac{1}{n} \sum_{i=1}^{n} (y_i - f(x_1(i), x_2(i), x_3(i)))^2 + \lambda J(f) \quad (2.25)$$

where n is the number of known reference sample points, $y_i$ is a value at such a sample point, $x1(i)$, $x2(i)$ and $x3(i)$ are the input coordinate values of sample i, and $\lambda$ is a smoothing parameter determining the effect the penalty function $J(f)$ will have on the final interpolation. $J(f)$ represents the bending energy of the thin plates. In three dimensions, this function is given by [38, p. 89].

$$J(f) = \int_{-\infty}^{\infty}\int_{-\infty}^{\infty}\int_{-\infty}^{\infty} \left(\frac{\partial^2 f}{\partial x_1^2}\right)^2 + \left(\frac{\partial^2 f}{\partial x_2^2}\right)^2 + \left(\frac{\partial^2 f}{\partial x_3^2}\right)^2 + 2\left[\left(\frac{\partial^2 f}{\partial x_1 x_2}\right)^2 + \left(\frac{\partial^2 f}{\partial x_1 x_3}\right)^2 + \left(\frac{\partial^2 f}{\partial x_2 x_3}\right)^2\right] dxdydz. \quad (2.26)$$

Duchon [32] showed that the interpolation function f minimizing 2.25 is of the form $$f(x) = a_1 + a_2 x_1 + a_3 x_2 + a_4 x_3 + \sum_{i=1}^{n} b_i U(|x - x(i)|) \quad (2.27)$$

where $U(r) = r^2 \log(r^2)$.

By defining a matrix K with elements $K_{ij} = (|x(i) - x(j)|)$ and a matrix $M = K + n\lambda I$, where I is the identity matrix, Wahba [33] shows that the equations above can be written as $$Mb + Ta = y$$

$$T'b = 0 \quad (2.28)$$

where a and b are vectors containing the coefficients in equation 2.27, y is a vector with values of the n reference samples, and T is a matrix of the form $$T = \begin{bmatrix} 1 & x_1(1) & x_2(1) & x_3(1) \\ 1 & x_1(2) & x_2(2) & x_3(2) \\ \cdots & \cdots & \cdots & \cdots \\ 1 & x_1(n) & x_2(n) & x_3(n) \end{bmatrix} \quad (2.29)$$

Equation 2.28 can thus be expressed in matrix form as $$\begin{bmatrix} M & T \\ T' & O(4,4) \end{bmatrix} \times \begin{bmatrix} b \\ a \end{bmatrix} = \begin{bmatrix} y \\ O(4,1) \end{bmatrix} \quad (2.30)$$

where $O(r, c)$ is a zero matrix. The values for the coefficients in vectors a and b are then calculated by inversing the $$\begin{bmatrix} M & T \\ T' & O(4,4) \end{bmatrix}$$

matrix. To include the calibration of all three dimensions in the above equation, vectors a, b and y can be extended to matrices with three columns of the form $[a_1\ a_2\ a_3]$. For a more rigorous mathematical development of the above relations, see, for example, chapter 2.4 of the book by Wahba [33].

Other calibration methods can also be used to calibrate the measured skin color to within an acceptable level, such as Kriging methods, or Partal Least-Squares Regression methods.

Test Methodology

A Samsung Galaxy S3 (GT-I9300, Samsung, South-Korea) and a HTC One V (One V, HTC, Taiwan) were used for this project. Compared to other smartphones, the S3 has a high quality camera [34], while the One V has a decent camera [35].

Several methods were tested using these two phones. They were tested on skin of a light color, type II on the Fitzpatrick skin type scale. For control purposes, numerical skin simulations and measurements of this skin with bruises were performed. The methods tested and the controls used are described below.

There exist a couple of methods to either simulate increased bilirubin concentration in the skin, or to obtain an actual higher skin bilirubin concentration. One of these methods is to perform measurements on bruised skin. The yellow color seen in or around bruises is, as mentioned earlier, caused by increased bilirubin concentration. Measurements on both yellow bruised skin and skin in close proximity to the bruise, but with no distinct yellow color, have been performed. This gives a qualitative result of whether the measurement method can separate skin with low bilirubin concentration from skin with higher concentrations.

The use of bruises allowed for a coarse test of whether the different measurement methods would work or not. However, quantitative results were also needed to test the accuracy of the promising methods. Therefore, numerical simulations of skin were performed. This allowed for the creation of both reflection spectra and simulated colors of skin with varying concentrations of, e.g., bilirubin and melanin. Simulations were performed using the three-layer diffusion model described earlier. Wavelengths were sampled at 5 nm intervals. The resulting simulated reflection spectra were then combined with a light source spectrum similar to one used during measurements, i.e., CIE standard illuminant D50 for daylight [44, p. 93].

The simulations were performed with a blood oxygenation level of the top and second skin layers of 0.5 and 0.8, respectively. The blood volume fractions of the top and second layer were set to 1%. The thickness of the top layer was set to 100 microns, while the thickness of the second layer was set to 250 microns. The water, fat, beta-carotene and methemoglobin levels were set to zero. The scattering coefficient was calculated with values as described in equation 2.3. Melanin concentrations were varied from an absorption at 694 nm of 250 $m^{-1}$ to 2000 $m^{-1}$. Bilirubin concentrations were varied from 0 micromolar to 200 micromolar.

An alternative to taking pictures and blood samples of a newborn and finding color correlations afterwards, is to attempt to predict the color of the newborn's skin with varying levels of bilirubin. These predictions can then be compared to measurements performed using a camera. This requires good numerical simulations to predict the skin colors, as well as cameras that are calibrated to reproduce the true colors of the captured scene. High-end digital cameras are today calibrated using images of, e.g., a Macbeth ColorChecker in RAW format. Free tools are available that can perform such a calibration, but no smartphones on the market today support RAW file output. For this reason, a different calibration procedure was needed.

To calibrate the smartphone cameras, pictures of a Macbeth ColorChecker (MacBeth ColorChecker, Munsell Color, Baltimore, USA) were taken. Most of these images were captured using diffuse daylight through a window as the light source. For these images, the colors given in a paper by Pascale [37] were used as the reference ColorChecker colors. Images were also captured using only the built-in flashlight of the smartphones as the light source. For those images, the reference ColorChecker colors were calculated from the reflection spectra of the ColorChecker and the light spectrum of the flashlights. The reflection spectra of the ColorChecker were gathered from the Munsell Color Science Laboratory website [37].

The pixel coordinates of the ColorChecker squares in the images were found manually. The colors of the squares were then calculated as the average of all the pixels in a square box centered on the squares pixel coordinate. The side lengths of these square boxes were set to 21 pixels, making the color of one of the ColorChecker squares the average of 441 pixels within that square. These colors were then converted to the xyY color space, as they could then be compared with the reference ColorChecker values.

Before calibration was attempted, the standard deviation of the color reproduction of the cameras was measured. This was done by taking 10 pictures of the ColorChecker from slightly different angles using diffuse daylight through a window as the light source. A series of ten pictures were taken using both daylight and auto white balance mode for both cameras. The colors of the squares were then found and converted to xyY. An estimate of the standard deviation of the xy chromaticity was then found by averaging the standard deviation of the x and y values of the 24 individual ColorChecker squares. The final standard deviation was then calculated as the vector sum of the x and y standard deviations, $\Delta xy = \text{sqrt}(\Delta x^2 + \Delta y^2)$.

Two calibration procedures were developed. The first is a generalized polynomial transform, which was reported as precise by researchers in the field of computer vision [28]. The other method is an implementation of the Thin-Plate Spline interpolation algorithm, which has been reported as a highly efficient calibration technique [29]. The theory behind the techniques is described earlier herein. Both methods were developed to be used for three color channels, i.e., the RGB and XYZ color spaces. The Thin-Plate Spline interpolation algorithm was later modified to also work using only two color channels, so that it could be used for calibration of xy chromaticity. The general polynomial transform was not modified in the similar way because the Thin-Plate Spline method had proven to be superior.

The efficiency of each of the two methods was tested using ordinary cross-validation. Ordinary cross-validation works by leaving one test sample out when creating a prediction model such as a general polynomial transform. The prediction model is then used to predict the value of the test sample that was left out during the model's creation. The error of this prediction therefore becomes an estimate of the accuracy of the prediction model. This procedure is repeated, leaving out a different test sample each repetition until all test samples have been left out once. The prediction errors of these repetitions are then averaged to give the estimate of the final model's prediction error. In the case where the test samples are the 24 colors of the Color-Checker, 24 prediction models were created, leaving one different color out for each model. These 24 models were then used to predict the value of the color that was left out during the creation of the model. The averages of the errors of these predictions were then used as an estimate of the error of the final prediction model created using all 24 colors.

Ordinary cross-validation was also used to optimize the calibration methods. For the general polynomial transform, the polynomial order could be changed to test, for example, whether a higher order would yield a more precise calibration. Finding the optimal order was quick and easy because increasing the order above three more often than not decreased the quality of the calibration. Thus, finding the optimum polynomial order involved running ordinary cross-validation for order one, two and three, and finding the polynomial order with the smallest error. The Thin-Plate Spline method, on the other hand, needed fine-tuning of the smoothing parameter λ which can be any number above or equal to zero (see equation 2.25). An iterative procedure was developed that first tested a range of values of A using ordinary cross validation. After this, a new range of values were tested centered on the value λ that showed the least error in the previous iteration. Using this method, a highly accurate estimation of the optimal value of λ was found after only 6 or 7 such iterations.

The calibration methods were tested on images taken using diffuse daylight through a window as the light source. Pictures of the ColorChecker were taken using all the different white balance settings on the cameras to find the best option. At the same time, pictures were taken of a bruised arm so that the calibration method could be compared to a real case of increased bilirubin as well as simulations. The colors of the pictures of the arm were then corrected using the calibrations calculated from the images of the ColorChecker. Then, the pixel coordinates of two points on the arm were found manually. First, a point where there was a clear yellow color from the bruise, and second, a point on the arm with no bruise or other clearly visible pigments such as moles. The color of these two points were then calculated as the average color of the colors inside a square with side lengths of 21 pixels centered around the points. These colors were then converted to xy chromaticities in order to compare them to numerical simulations and the calibration quality.

Calibration was, as mentioned earlier, also performed on pictures of the ColorChecker captured using the built-in flashlight on the smartphones as the only light source. This was done because the reference colors of the ColorChecker given in the paper by Pascale [36] were calculated using D50 as the light source. D50 is a good daylight simulator, but it is highly likely that there is some deviation from the true colors of the ColorChecker. To calculate the true colors of the ColorChecker using the flashlights, their light spectra were measured using the SD2000 spectrometer with the SpectraSuite computer app. A 10 millisecond integration time was used along with smoothing by using the average of ten spectra as the resulting spectrum. In addition, the color spectrum of the flashlight on an iPhone 5 was also measured to see if there is a large variance in different smartphone flashlights. These spectra could then be combined with the reflection spectra of the ColorChecker [37] to get the true colors of the ColorChecker.

Results

Figure 5:
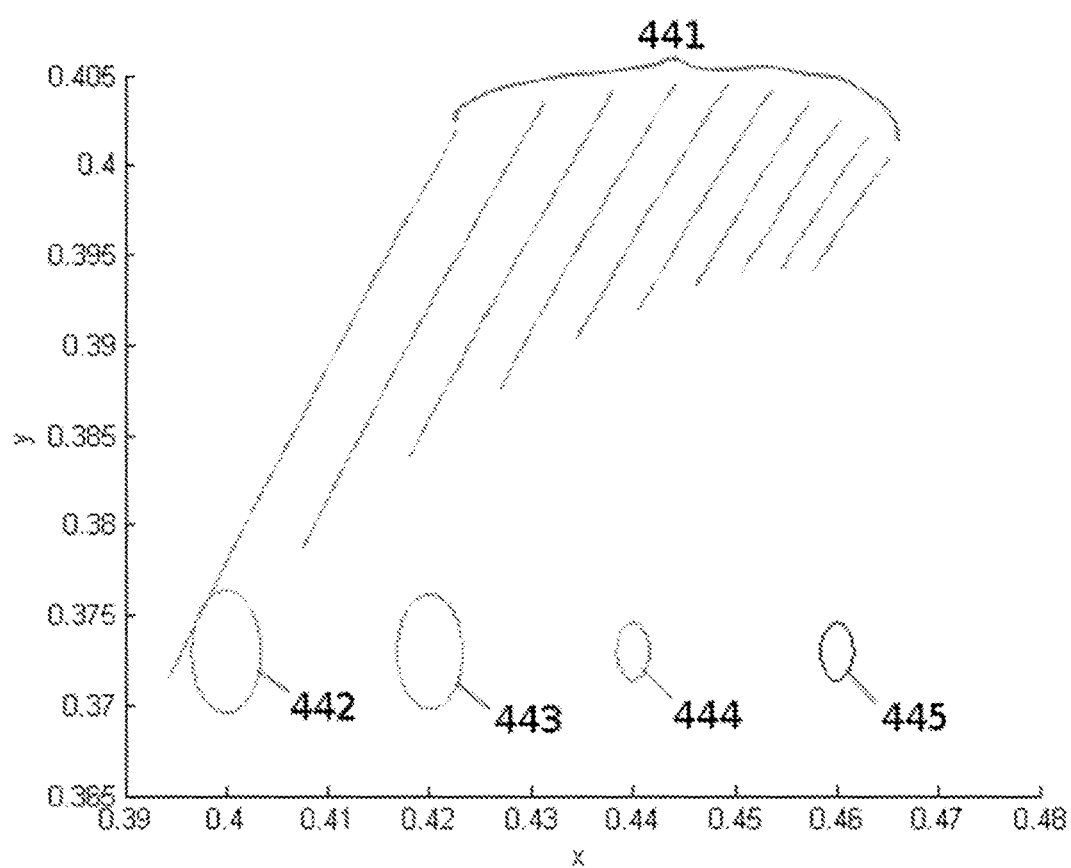
FIG. 5 shows standard deviation of the cameras plotted with skin simulation results.

The standard deviation of the color reproduction of the HTC was estimated to be 0.0036 for the auto white balance setting in the xy color coordinates. For the daylight white balance setting, it was estimated to 0.0034. Both white balance settings resulted in a standard deviation of 0.0016 using the Samsung. These standard deviations are illustrated in FIG. 5, where the standard deviation is seen as the radius of the circles 442-445 in the figure. The lines 441 in the figure represent a series of simulations with increasing concentrations of bilirubin, from 0 micromolar at the bottom left of the line to 200 micromolar at the top right. Each line to the right of another is another series of simulations of increasing bilirubin, but for a higher concentration of melanin. The absorption of melanin at 694 nm is 250 m$^{-1}$ for the leftmost line, and 2000 m$^{-1}$ for the rightmost line.

The size of the circles 442-445 in FIG. 5 can be compared to the length of the lines 441 as an indicator of whether the camera's color variance is low enough to be able to separate skin with high concentrations of bilirubin from skin with lower concentrations. This appears to be true for both cameras, except for the HTC when compared to simulations with very high melanin concentrations.

Before color calibration was performed on the images, the average error of the measured colors of the ColorChecker was usually between 50 and 60, measured as the vectorial color distance in RGB color space. Using the general polynomial transform to color calibrate the images, this error was reduced to approximately 30. The Thin-Plate Spline interpolation, on the other hand, managed to decrease the error to approximately 25. Using the Thin-Plate Spline interpolation on the images in xy coordinates yields prediction errors of 0.0126 and 0.0275 for the HTC with the white balance set to auto and daylight, respectively. For the Samsung, the prediction errors were 0.0157 and 0.0163 with the same white balance settings. These values are plotted in FIG. 6 similarly to the standard deviations plotted in FIG. 5. The reason for the large value of the calibration error of the HTC with white balance set to daylight is not known. Prediction errors were also calculated for the other white balance settings, but auto and daylight were the ones with the best results for the images captured with diffuse daylight through a window as the light source.

Figure 6:
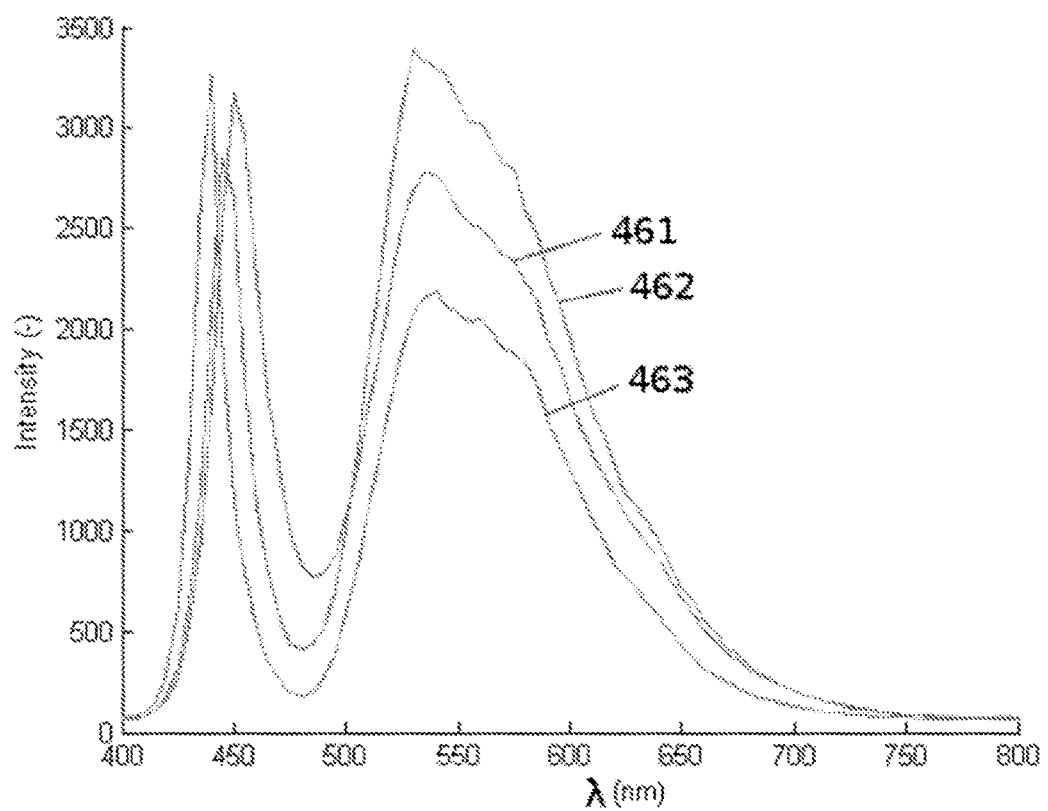
FIG. 6 shows predicted error of the calibration plotted with skin simulation results.

The diameter of the circles 452-455 in FIG. 6 are of approximately the same length as the length of the lines 451. This indicates that this calibration procedure is not precise enough for bilirubin concentrations to be estimated from comparing a color measurement to numerical simulations. A calibration improvement was seen when the images were taken using the flashlight of the phones as the light source. When the reference colors from the paper by Pascale [36] were used to calibrate the images taken using the flashlights, the results were prediction errors of 0.015 and 0.023 for the HTC and Samsung, respectively. Using the colors of the ColorChecker calculated by combining the flashlight spectra and the reflection spectra of the ColorChecker, calibration errors were reduced to 0.012 and 0.018, an improvement of approximately 20%. These errors have been further decreased using Kriging methods and by correcting for light intensity variations as described in the following paragraphs concerning the color calibration card.

Gaussian process regression is a regression method used to generate both good predictions of values at unknown inputs, but also to get an estimate of the error at that point. Other regression methods can create uncertainty estimates through, e.g., cross validation, which creates an error measurement based on the predicted values at certain known points. Gaussian process regression is able to create error estimates for all points in the input space, including the exact point being measured.

Gaussian process regression has also provided the best color calibration of the methods that have been tested. This, in addition to providing an error estimate at the point that is measured, makes it the preferred calibration method. For a general introduction of Gaussian process regression, see, for example, Ebden [43]. For a detailed guide to Gaussian process regression with uncertain inputs, as used here, see, for example, chapter 3 of Girard [44].

Figure 7:
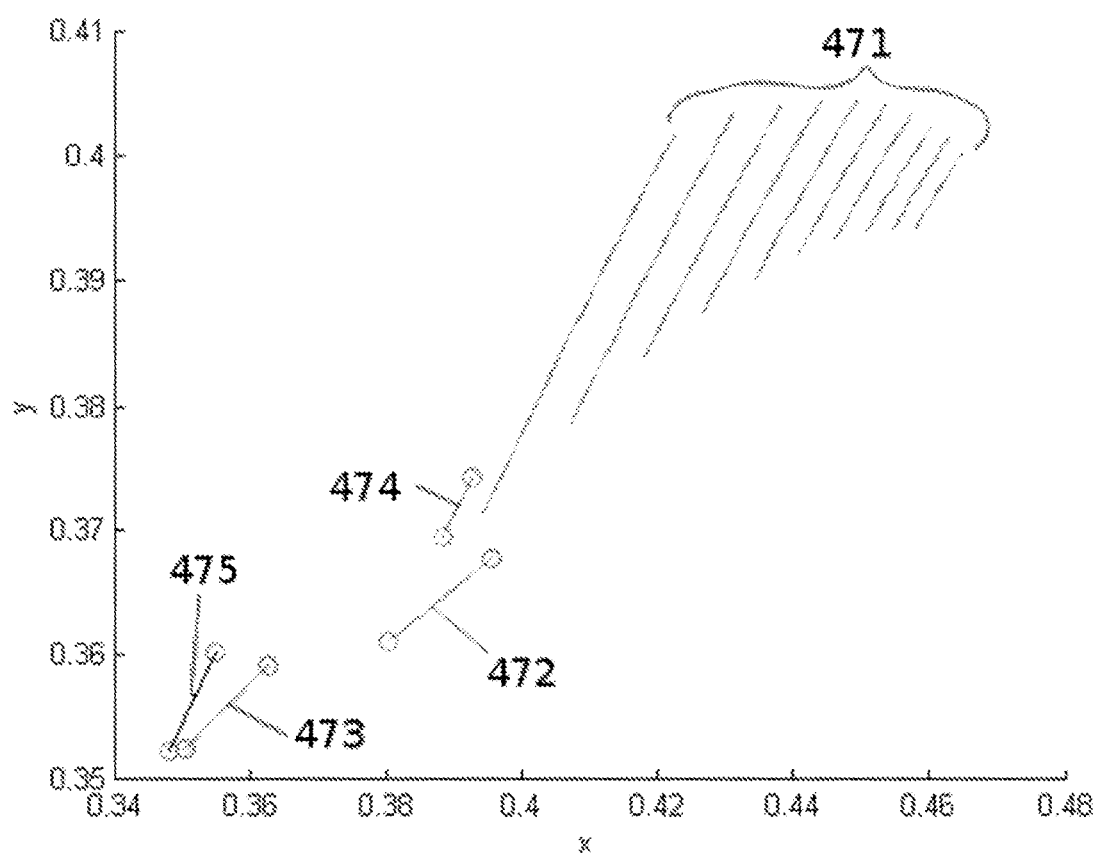
FIG. 7 shows light intensity spectra of flashlights of three different phones.

The measured flashlight spectra can be seen in FIG. 7. All spectra are very similar and share the same characteristic shape. This makes it likely that most smartphones use the same type of diodes in their flashlights, sharing a similar spectrum.

Figure 8:
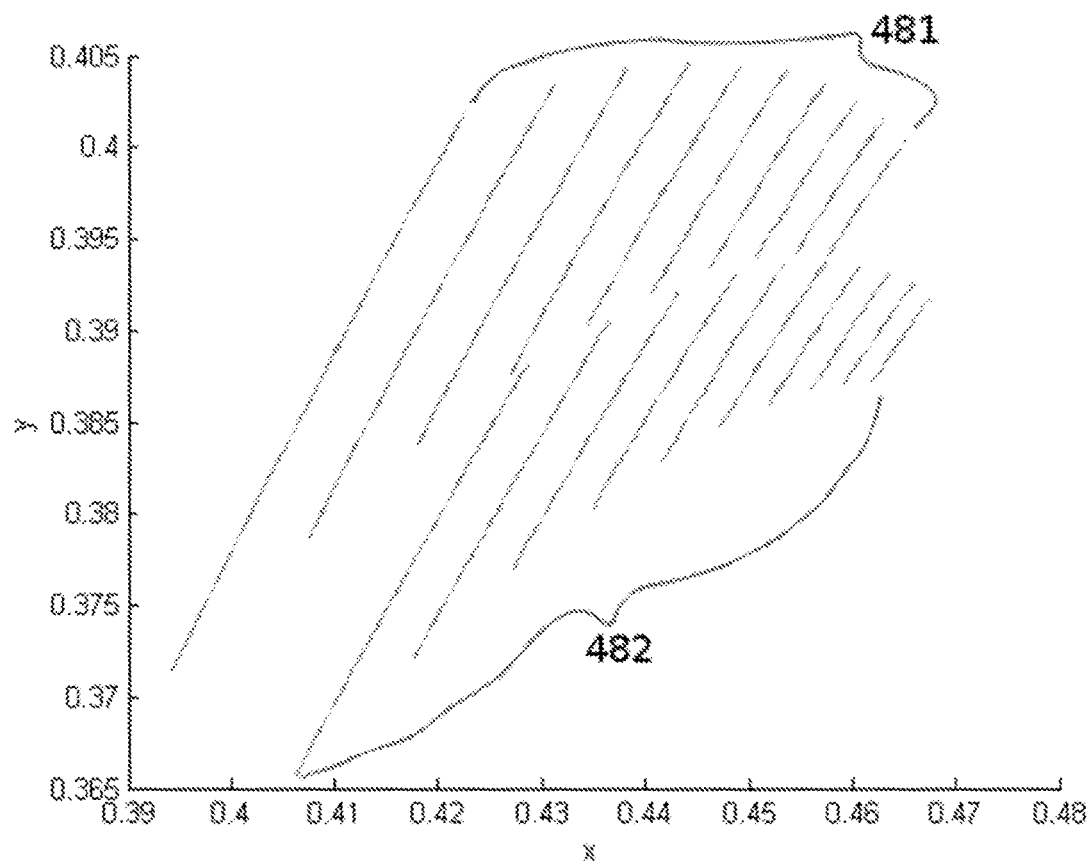
FIG. 8 shows color measurements of skin plotted with skin simulation results.

Color measurements of skin with and without a bruise were also performed using the same calibrations as were used for the prediction errors shown in FIG. 6. These measurements can be seen in FIG. 8. Each line with two connected circles 472-475 represents two color measurements. The bottom left circles of 472-475 indicate a color measurement done on skin with no bruise. The upper right circles of 472-475 indicate measurements done on a bruise. The lines 471 represent simulations as before. All the lines 472-475 going from a measurement of the skin to a measurement of the skin with a bruise point up to the right similarly to the numerical simulations of increasing bilirubin concentrations. This indicates that the calibrated color measurements are indeed capable of measuring increased bilirubin concentrations.

The purpose of the color calibration is to make the cameras able to measure the true colors of the scene they are capturing. These captured colors can then be compared to numerical simulations of skin color to give an estimate of the bilirubin concentration of the skin. FIG. 5 shows that the standard deviation of the cameras is small enough that this is possible. If this had not been the case, several images of the target could have been captured and the means of the captured color values could have been used instead. This technique can of course be used when the standard deviation is small as well, as a means of reducing the errors caused by the camera itself. The results of the calibration procedures in FIG. 6, on the other hand, show a far larger error than can be accepted if bilirubin concentrations are to be measured. A remedy for this is suggested by Menesatti et al.

Menesatti et al. [35, p. 12] reports that when using the Thin-Plate Spline interpolation method, the use of Color-Checkers with more color patches results in calibrations of higher accuracy than calibrations performed with fewer color patches. In addition, the method showed that the farther away the measured color was from the closest reference patch color, the larger the calibration error. For this reason, the use of ColorCheckers with several colors that closely match the colors of interest was suggested, to reduce calibration error. ColorCheckers could even be created and printed ad hoc, and the colors could then be measured a posteriori using a spectrometer.

Numerical skin simulations have been used to calculate the whole range of skin colors expected to exist in newborns. Skin colors to be used as reference color points on the calibration card have been chosen by choosing colors that maximise the distance between them. This ensures that when the skin color of newborns is measured, the distance between the measured color and the colors on the calibration card will be minimal, increasing the accuracy of the proceeding calibration algorithms.

The colors on the calibration card may be printed using a process known as spectral printing [36]. Spectral printing tries to replicate the entire reflection spectrum of light, instead of just the RGB color. An advantage of using spectral printing is that the measured colors of the calibration card will change in a similar fashion to the measured color of the skin when the light source illuminating the card and skin changes. Without using spectral printing, there is no guarantee that the printed color remains similar to a skin color when the light source or the illumination changes. Using spectral printing is therefore an advantage when creating a system that can be used in different light conditions or using different illumination sources. Typically, seven color components are used in spectral printing. In some embodiments, there may be fewer than seven color components to save cost of the calibration card. In other embodiments, there may be more than seven color components, to allow control of the changes of the colors of the calibration card under changing illumination conditions. An advantage with spectral printing of the calibration card is that it is possible to manufacture a calibration card that behaves similar to skin, sclera or area of the body under the same illumination conditions.

Typically, the calibration card is made of cardboard or paper. The calibration card may have an opening or transparent section through which the skin, sclera or an area of the body would be visible. Preferably, the calibration card is not transparent. The calibration card may be made of plastic or other material that provides sufficient stiffness in such a way that the calibration card does not easily bend or deform.

Figure 9:
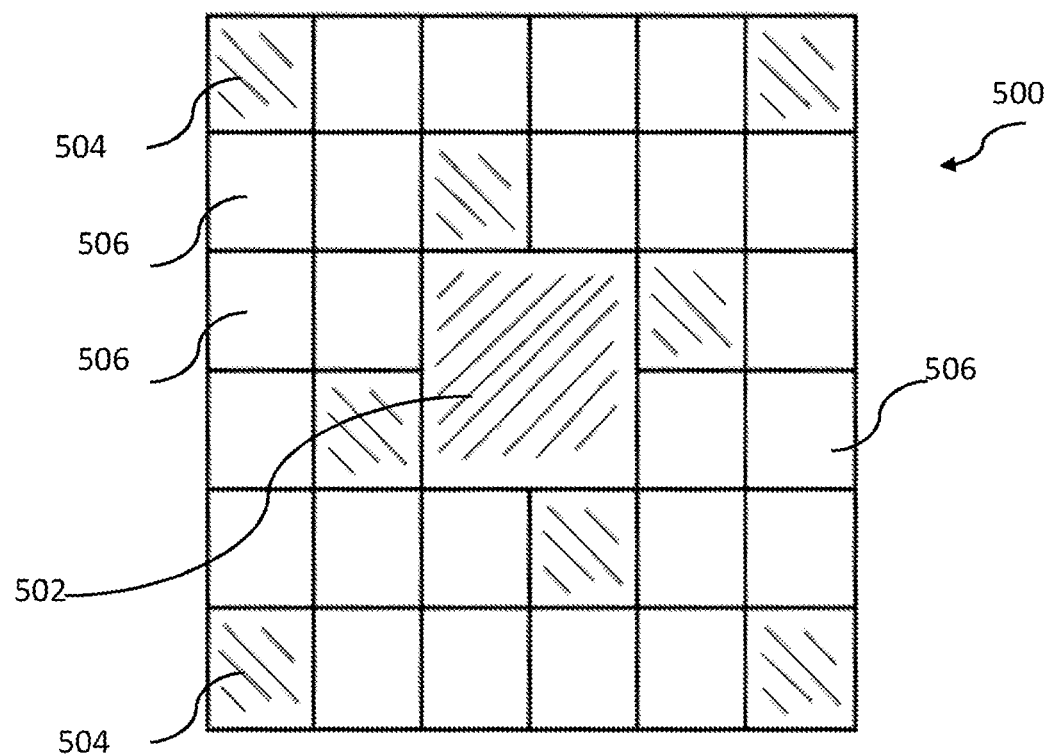
FIG. 9 shows a first embodiment of a color calibration card.

FIG. 9 shows a first embodiment of a color calibration card 500 with grey patches 504 for light source strength correction. Rectangles with the number 504 indicate grey rectangles used for light source strength correction. They are evenly distributed to ensure that all colored patches and skin is adjacent to at least one grey color patch. Rectangles with the numbers 506 indicate colored rectangles which are used for color calibration. The color of the colored rectangles may be chosen among suitable skin colors, simulated skin colors or other colors suitable for calibration of images. The colored rectangles 506 may have different colors, or some of the colored rectangles may have similar color. In an embodiment of the calibration card, the colored patches 506 are comprised of 24 different colors. The rectangle with the number 502 indicates the opening in the calibration card through which the skin will be visible. If there, for some reason, is no need for light source strength correction for a certain app, the grey patches can be replaced by more colored patches.

Figure 10:
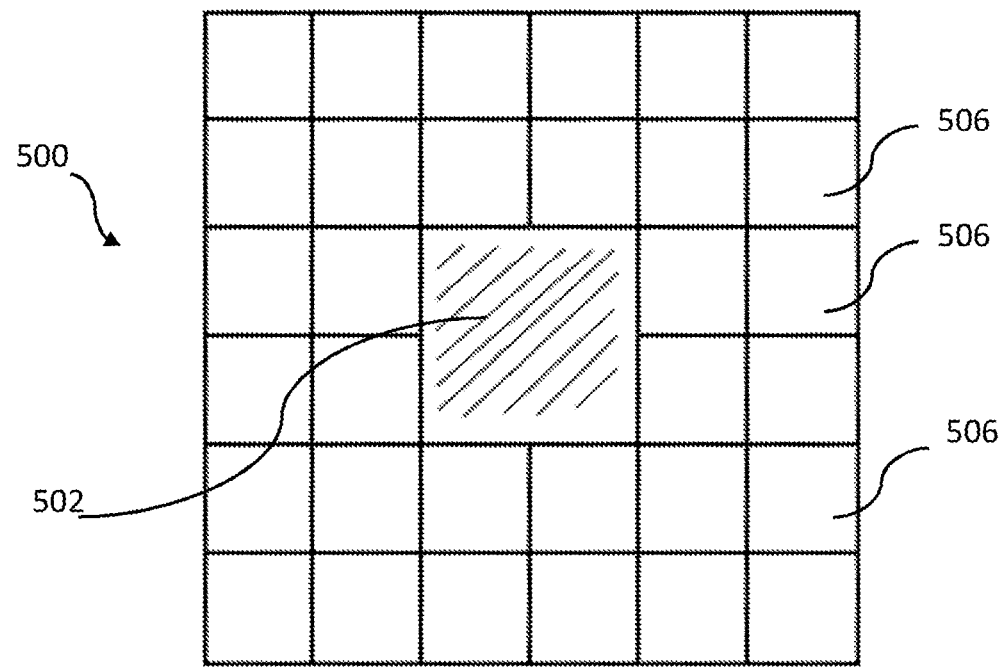
FIG. 10 shows a second embodiment of a color calibration card.

FIG. 10 shows another embodiment of a color calibration card 500. Rectangles with the numbers 506 indicate colored rectangles which are used for color calibration. The color of the colored rectangles may be chosen among suitable skin colors, simulated skin colors or other colors suitable for calibration of images. The colored rectangles 506 may have different colors, or some of the colored rectangles may have similar color. In an embodiment of the calibration card, the colored patches 506 is comprised of 24 different colors. The rectangle with the number 502 indicates the opening in the calibration card through which the skin will be visible. If there, for some reason, is no need for light source strength correction for a certain app, the grey patches can be replaced by more colored patches.

In other embodiments of the calibration card, there may be no opening, or the opening may be located at the periphery of the calibration card.

Preferably, when photographing the skin, sclera or other area of the body, the calibration card is part of the image.

The grey colors on the calibration card are used to correct any variation in light source strength across the imaged calibration card. When using a flash or ambient lighting as the light source, there is no guarantee that very part of the calibration is illuminated with the same intensity. By having grey calibration patches with the same color across the card, the light source strength can be modeled across the card and correct for any variation. This technique may be used both with calibration cards printed using spectral printing, and with calibration cards printed using traditional printing techniques.

In addition to skin colors on the calibration card chosen from the numerical skin simulations described above, the calibration card may include some grey patches. These grey patches should be as similar as possible, as they are used to correct for any variation in the illumination across the calibration card. Using the fact that the grey patches should reflect the same color regardless of where they are situated on the calibration card, the variation in the reflected color from these patches can be used to correct for light intensity variation on to the color patches and on to the skin. Several different algorithms could be used to perform this correction, such as bilinear interpolation, linear regression, Gaussian process regression methods, etc.

This method could possibly also be used as a diagnostic tool for other conditions. As discussed above, the reflection spectrum of newborn skin can be used to calculate more than the bilirubin concentration. The color of the skin is a result of the reflection spectrum, and could therefore be used to calculate some of the same parameters, even though most of the spectral information is lost when the reflection spectrum is collapsed to three color values. Takiwaki and Serup [39] found such color indicators on psoriatic plaque, opening the possibility of using color analysis to diagnose psoriasis, or at least to measure the extent of it. However, the technique is not limited to the medical field. The color measurement technique may be used to objectively measure the color of, e.g., paint, or custom color calibration cards may be produced to assess the color quality of food in factories and stores, etc. The apps mentioned here should not be seen as an exhaustive list.

One embodiment is to depict the skin using a smartphone and the smartphone's flash with a custom made color calibration card with colors selected from numerical skin simulations and printed using spectral printing placed on the skin. The skin color is then calibrated using a Gaussian process regression method, and compared with simulated skin colors and corresponding bilirubin concentrations in a direct lookup table. This gives a good estimation of the bilirubin concentration from the measurement of skin color.

The calibration card needs to be as close possible to the area of the skin, sclera or other area that is to be analyzed. Placing the calibration card close to the area to be analyzed ensures that the same lighting conditions exist on the calibration card as the skin/sclera being measured. One way to get the card close to the area that needs to be analyzed is to have an opening in the calibration card. The calibration card is then placed on a child's chest when measuring the skin, or held near the eye of the child when measuring sclera.

A number of variations on the above can be envisaged. For instance, also sclera of the eyes can be used, using a similar model. Since jaundice affects the eyes at a delayed rate from the skin, it is possible with one set of measurements to determine if the level of bilirubin is increasing or decreasing. Thus, if the level of bilirubin is increasing, the analysis using skin gives a higher indication than for sclera. At steady state, both give the same indication.

The estimation of a bilirubin concentration from the calibrated skin color measurement can also be performed by a meta model instead of a direct lookup table. The accuracy of this estimation may be improved by finding which input skin parameters to the model are most likely with regard to the measured color. The color calibration can also be performed by other algorithms than the Thin-plate Spline method, for example by partial least squares regression or Gaussian process regression. In addition, calibration can be improved by using both an image captured without flash and an image captured with flash. Calibration can also be performed on a single image captured without flash.

The calibration card may be manufactured of a stiff and transparent material like Plexiglas. The calibration colors are printed on the transparent material. The calibration card may be pressed towards the skin and thereby providing an even and flat surface that may be imaged.

The calibration card may be equipped with light sources to provide calibrated illumination of the skin, sclera or other part of the body. This would be advantageous in having a known illumination source.

In other embodiments, the calibration card may be replaced with light projected on the skin, sclera or an area of the body. The light may be projected from a known light source like video projector, screen of a smartphone, flash or other suitable light source. The screen of a smartphone may be used for illumination where a specific light pattern is shown on the display, and when in proximity of the skin, the light from the display is reflected from the skin and captured by the camera in the smartphone.

REFERENCES

[1] Tina M. Slusher, Alvin Zipursky, and Vinod K. Bhutani. A global need for affordable neonatal jaundice technologies. Seminars in Perinatology, 35(3):185-191, June 2011. Available from: http://linkinghub.elsevier.com/retrieve/pii/S0146000511000437, doi:10.1053/j.semperi.2011.02.014.

[2] Vinod K. Bhutani, Alvin Zipursky, Hannah Blencowe, Rajesh Khanna, Michael Sgro, Finn Ebbesen, Jennifer Bell, Rintaro Mori, Tina M. Slusher, Nahed Fahmy, Vinod K. Paul, Lizhong Du, Angela A. Okolo, Maria-Fernanda de Almeida, Bolajoko O. Olusanya, Praveen Kumar, Simon Cousens, and Joy E. Lawn. Neonatal hyperbilirubinemia and rhesus disease of the new-born: incidence and impairment estimates for 2010 at regional and global levels. Pediatric Research, 74:86-100, December 2013. Available from: http://www.nature.com/doifinder/10.1038/pr.2013.208, doi:10.1038/pr.2013.208.

[3] Tina M Slusher, Bolajoko O Olusanya, Hendrik J Vreman, Ronald J Wong, Ann M Brearley, Yvonne E Vaucher, and David K Stevenson. Treatment of neonatal jaundice with filtered sunlight in nigerian neonates: study protocol of a non-inferiority, randomized controlled trial. Trials, 14:446, 2013. doi: 10.1186/1745-6215-14-446.

[4] V A Moyer, C Ahn, and S Sneed. Accuracy of clinical judgment in neonatal jaundice. Archives of pediatrics & adolescent medicine, 154(4):391-394, April 2000.

[5] A Carceller-Blanchard, J Cousineau, and E E Delvin. Point of care testing: transcutaneous bilirubinometry in neonates. Clinical biochemistry, 42(3):143-149, February 2009. doi:10.1016/j.clinbiochem.2008.09.106.

[6] A N Bashkatov, E A Genina, V I Kochubey, and V V Tuchin. Optical properties of human skin, subcutaneous and mucous tissues in the wavelength range from 400 to 2000 nm. Journal of Physics D: Applied Physics, 38(15):2543-2555, August 2005. Available from: http://stacks.iop.org/0022-3727/38/i=15/a=004?key=crossref.33282f5 2c8be33f7c28513be248e8c27, doi:10.1088/0022-3727/38/15/004.

[7] R. Rox Anderson and John A. Parrish. The optics of human skin. Journal of Investigative Dermatology, 77(1):13-19, July 1981. Available from: http://www.nature.com/jid/journal/v77/n1/abs/5615637a.html, doi:10.1111/1523-1747.ep12479191.

[8] Fitzpatrick T B. The validity and practicality of sunreactive skin types I through VI. Archives of Dermatology, 124(6):869-871, June 1988. Available from: http://dx.doi.org/10.1001/archderm.1988.01670060015008, doi:10.1001/archderm.1988.01670060015008.

[9] M. L. Wolbarsht, A. W. Walsh, and G. George. Melanin, a unique biological absorber. Applied Optics, 20(13):2184-2186, 1981. Available from: http://www.opticsinfobase.org/ao/fulltext.cfm?uri=ao-20-13-2184.

[10] L. T. Norvang, T. E. Milner, J. S. Nelson, M. W. Berns, and L. O. Svaasand. Skin pigmentation characterized by visible reflectance measurements. Lasers in Medical Science, 12(2):99-112, June 1997. Available from: http://link.springer.com/article/10.1007/BF02763978, doi:10.1007/BF02763978.

[11] Rashmi Sarkar, Srikanta Basu, R. K. Agrawal, and Piyush Gupta. Skin care for the newborn. Indian pediatrics, 47(7):593-598, 2010. Available from: http://link.springer.com/article/10.1007/s13312-010-0132-0.

[12] Rachel Ash-Bernal, Robert Wise, and Scott M. Wright. Acquired methemoglobinemia: A retrospective series of 138 cases at 2 teaching hospitals. Medicine September 2004, 83(5):265-273, 2004. Available from: http://ovid-sp.ovid.com/ovidweb.cgi?T=JS&CSC=Y&NEWS=N&PAGE=fulltext&D=ovftg&AN=00005792-200409000-00001.

[13] Janelle E. Phelps, Karthik Vishwanath, Vivide T. C. Chang, and Nirmala Ramanujam. Rapid ratiometric determination of hemoglobin concentration using UV-VIS diffuse reflectance at isosbestic wavelengths. Optics Express, 18(18):18779-18792, August 2010. Available from: http://www.ncbi.nlm.nih.gov/pmc/articles/PMC3093134/, doi:10.1364/OE.18.018779.

[14] A F McDonagh and D A Lightner. 'Like a shrivelled blood orange'-bilirubin, jaundice, and phototherapy. Pediatrics, 75(3):443-455, March 1985.

[15] N. E. I. Langlois and G. A. Gresham. The ageing of bruises: A re-view and study of the color changes with time. Forensic Science International, 50(2):227-238, September 1991. Available from: http://www.sciencedirect.com/science/article/pii/037907389190154B, doi:10.1016/0379-0738(91)90154-B.

[16] Neville R. Pimstone, Raimo Tenhunen, Paul T. Seitz, Harvey S. Marver, and Rudi Schmid. The enzymatic degradation of hemoglobin to bile pigments by macrophages. The Journal of Experimental Medicine, 133(6):1264-1281, June 1971. Available from: http://jem.rupress.org/content/133/6/1264, doi:10.1084/jem.133.6.1264.

[17] T. W. R. Hansen and D. Bratlid. Bilirubin and brain toxicity. Acta Pdiatrica, 75(4):513-522, July 1986. Available from: http://onlinelibrary.wiley.com/doi/10.1111/j.1651-2227.1986.tb10242.x/abstract, doi:10.1111/j.1651-2227.1986.tb10242.x.

[18] Vinod K. Bhutani, Glenn R. Gourley, Saul Adler, Bill Kreamer, Chris Dalin, and Lois H. Johnson. Noninvasive measurement of total serum bilirubin in a multiracial predischarge newborn population to assess the risk of severe hyperbilirubinemia. Pediatrics, 106(2):e17-e17, August 2000. Available from: http://pediatrics.aappublications.org/content/106/2/e17.

[19] Steven L Jacques, David G Oelberg, and Iyad Saidi. Method and apparatus for optical measurement of bilirubin in tissue, October 1994. Available from: http://www.google.com/patents/US5353790.

[20] L. Lyngsnes Randeberg, E. Bruzell Roll, L. T. Norvang Nilsen, T. Christensen, and L. O. Svaasand. In vivo spectroscopy of jaundiced newborn skin reveals more than a bilirubin index. Acta Pdiatrica, 94(1):65-71, 2005. Available from: http://onlinelibrary.wiley.com/doi/10.1111/j.1651-2227.2005.tb01790.x/abstract, doi:10.1111/j.1651-2227.2005.tb01790.x.

[21] Robin M. Pope and Edward S. Fry. Absorption spectrum (380?700 nm) of pure water. II. integrating cavity measurements. Applied Optics, 36(33):8710-8723, November 1997. Available from: http://ao.osa.org/abstract.cfm?URI=ao-36-33-8710, doi:10.1364/AO.36.008710.

[22] L. O. Svaasand, L. T. Norvang, E. J. Fiskerstrand, E. K. S. Stopps, M. W. Berns, and J. S. Nelson. Tissue parameters determining the visual appearance of normal skin and port-wine stains. Lasers in Medical Science, 10(1): 55-65, March 1995. Available from: http://link.springer.com/article/10.1007/BF02133165, doi:10.1007/BF02133165.

[23] Akira Ishimaru. Diffusion of light in turbid material. Applied Optics, 28(12):2210, June 1989. Available from: http://www.opticsinfobase.org/ao/fulltext.cfm?uri=ao-28-12-2210&id=32482,doi:10.1364/AO.28.002210.

[24] Richard C. Haskell, Lars O. Svaasand, Tsong-Tseh Tsay, Ti-Chen Feng, Matthew S. McAdams, and Bruce J. Tromberg. Boundary conditions for the diffusion equation in radiative transfer. JOSA A, 11(10):2727-2741, 1994. Available from: http://www.opticsinfobase.org/abstract.cfm?id=841.

[25] Thorsten Spott and Lars O. Svaasand. Collimated light sources in the diffusion approximation. Applied Optics, 39(34):6453, December 2000. Available from: http://8.18.37.105/ao/abstract.cfm?uri=ao-39-34-6453, doi:10.1364/AO.39.006453.

[26] T. Smith and J. Guild. The C.I.E. colorimetric standards and their use. Transactions of the Optical Society, 33(3): 73, January 1931. Available from: http://iopscience.iop.org/1475-4878/33/3/301, doi:10.1088/1475-4878/33/3/301.

[27] C. S. McCamy, H. Marcus, and J. G. Davidson. A color-rendition chart. Journal of Applied Photographic Engineering, 2(3):95-99, 1976.

[28] Adrian Ilie and Greg Welch. Ensuring color consistency across multiple cameras. In Computer Vision, 2005. ICCV 2005. Tenth IEEE International Conference on, volume 2, page 1268-1275. IEEE, 2005. Available from: http://ieeexplore.ieee.org/xpls/abs_all.jsp?arnumber=1544866.

[29] Paolo Menesatti, Claudio Angelini, Federico Pallottino, Francesca Antonucci, Jacopo Aguzzi, and Corrado Costa. RGB color calibration for quantitative image analysis: The "3D thin-plate spline" warping approach. Sensors, 12(12):7063-7079, May 2012. Available from: http://www.mdpi.com/1424-8220/12/6/7063/,doi:10.3390/s120607063.

[30] Fred L. Bookstein. Principal warps: thin-plate splines and the decomposition of deformations. IEEE Transactions on Pattern Analysis and Machine Intelligence, 11(6): 567-585, June 1989. doi:10.1109/34.24792.

[31] Malcolm H. Davis, Alireza Khotanzad, Duane P. Flamig, and Steven E. Harms. A physics-based coordinate transformation for 3-d image matching. Medical Imaging, IEEE Transactions on, 16(3):317-328, 1997. Available from: http://ieeexplore.ieee.org/xpls/abs_all.jsp?arnumber=585766.

[32] Jean Duchon. Splines minimizing rotation-invariant semi-norms in sobolev spaces. In Prof Dr Walter Schempp and Prof Dr Karl Zeller, editors, Constructive Theory of Functions of Several Variables, number 571 in Lecture Notes in Mathematics, pages 85-100. Springer Berlin Heidelberg, January 1977. Available from: http://link.springer.com/chapter/10.1007/BFb0086566.

[33] Grace Wahba. Spline Models for Observational Data. SIAM, September 1990.

[34] TEST: samsung galaxy s III (s3)—multimedia. Available from: http://www.amobil.no/artikler/samsung-galaxy-s-iii-s3/109432.

[35] TEST: HTC one v—multimedia. Available from: http://www.amobil.no/artikler/htc-one-v/110020.

[36] 'Spectral Printing'. Wikipedia, 16 Jun. 2016. https://en.wikipedia.org/w/index.php?title=Spectral_printing&oldid=725497925.

[37] Danny Pascale. RGB coordinates of the macbeth ColorChecker. 2006. Available from: http://www.babelcolor.com/download/RGB%20Coordinates%20of%20the%20Macbeth%20ColorChecker.pdf.

[38] Useful color data. Available from: http://www.rit.edu/cos/colorscience/rc_useful_data.php.

[39] Hirotsugu Takiwaki and Jørgen Serup. Measurement of color parameters of psoriatic plaques by narrow-band reflectance spectrophotometry and tristimulus colorimetry. Skin Pharmacology and Physiology, 7(3):145-150, 1994. Available from: http://www.karger.com/Article/Abstract/211289, doi:10.1159/000211289.

[40] Tøndel, Kristin, and Harald Martens. "Analyzing Complex Mathematical Model Behavior by Partial Least Squares Regression-Based Multivariate Metamodeling: Mathematical Model Behavior by Partial Least Squares Regression-Based Multivariate Metamodeling." *Wiley Interdisciplinary Reviews: Computational Statistics* 6, no. 6 (November 2014): 440-75. doi:10.1002/wics.1325.

[41] Berget, Ingunn, Bjørn-Helge Mevik, and Tormod Naes. "New Modifications and Applications of Fuzzy-Means Methodology." Computational Statistics & Data Analysis 52, no. 5 (Jan. 20, 2008): 2403-18. doi:10.1016/j.csda.2007.10.020.

[42] Tøndel, Kristin, Ulf G Indahl, Arne B Gjuvsland, Jon Olav Vik, Peter Hunter, Stig W Omholt, and Harald Martens. "Hierarchical Cluster-Based Partial Least Squares Regression (HC-PLSR) Is an Efficient Tool for Metamodelling of Nonlinear Dynamic Models." *BMC Systems Biology* 5 (Jun. 1, 2011): 90. doi:10.1186/1752-0509-5-90.

[43] Solar spectrum calculator. Available from: https://www.pvlighthouse.com.au/calculators/solar%20spectrum%20calculator/solar%20spectrum%20calculator.aspx

[44] M. Ebden, arXiv:1505.02965 [Math, Stat] (2015)

[45] A. Girard, Approximate Methods for Propagation of Uncertainty with Gaussian Process Models (Citeseer, 2004).

The invention claimed is:

1. A method for estimating a level of bilirubin in blood causing jaundiced skin in a subject, the method comprising:
receiving a depiction of skin using an RGB sensor, and
determining a level of bilirubin in the depiction by comparing simulated skin colors of known bilirubin concentration with the received depiction, wherein the simulated skin colors are obtained by using one of, an optical diffusion model of a skin and Monte Carlo simulations of skin optics.

2. The method according to claim 1, wherein the depiction of skin is further color calibrated using a color calibration chart.

3. A method for determining a rate of change in a level of bilirubin in blood causing jaundiced skin and sclera, the method comprising:
receiving a depiction of jaundiced skin and sclera using an RGB sensor, calculating a level of bilirubin for skin and sclera in the received depiction by comparing simulated skin colors of known bilirubin concentration with the received depiction, wherein the simulated skin colors are obtained by using one of, an optical diffusion model of a skin and Monte Carlo simulations of skin optics, comparing the calculated level of bilirubin from the skin with the calculated level of bilirubin from the sclera, and determining a rate of change in the level of bilirubin in the blood by the difference in the indicated level of bilirubin from the skin to the indicated level of bilirubin from the sclera.

4. An apparatus for estimating a level of bilirubin in blood causing jaundiced skin in a subject, the apparatus comprising:

a receiving device configured to receive a depiction of skin using an RGB sensor, a calculating device configured to calculate simulated skin colors by using one of, an optical diffusion model of a skin and Monte Carlo simulations of skin optics, and a determining device configured to determine a level of bilirubin concentration in the blood by comparing the calculated simulated skin colors with the received depiction.

5. The apparatus according to claim 4, wherein the depiction further comprises a color calibration chart for color calibration of the depiction.

6. The method according to claim 2, wherein the calibration chart comprises a plurality of color patches and wherein the color patches are printed using spectral printing.

7. The method according to claim 6, wherein the calibration chart further comprises an opening through which the skin or sclera is visible.

8. The method according to claim 7, wherein the calibration chart further comprises a plurality of grey patches for detecting the variations of illumination of the calibration chart.

9. The method according to claim 8, wherein the grey patches are evenly distributed over the calibration chart.

10. The method according to claim 8, wherein at least one of the plurality of grey patches is arranged at a corner of the calibration chart.

11. The method according to claim 7, wherein at least one of the plurality of grey patches is colored with a simulated skin color with a corresponding bilirubin concentration.

12. The apparatus according to claim 5, wherein the calibration chart comprises a plurality of color patches, wherein the color patches on the calibration chart are printed using spectral printing.

13. The apparatus according to claim 12, wherein the calibration chart further comprises an opening through which the skin or sclera is visible.

14. The apparatus according to claim 13, further comprising a plurality of grey patches for detecting the variations of illumination of the calibration chart.

15. The apparatus according to claim 14, wherein the grey patches are evenly distributed over the calibration chart.

16. The apparatus according to claim 14, wherein at least one grey patch is arranged at a corner of the calibration chart.

17. The apparatus according to claim 15, wherein at least one of the plurality of grey patches is arranged at a corner of the calibration chart.

18. The apparatus according to claim 5, wherein at least one patch is colored with a simulated skin color with a corresponding bilirubin concentration.

* * * * *